(12) United States Patent
Sangar et al.

(10) Patent No.: US 7,951,985 B2
(45) Date of Patent: May 31, 2011

(54) PRODUCTION OF AROMATICS FROM METHANE

(75) Inventors: Neeraj Sangar, League City, TX (US); Larry L. Iaccino, Seabrook, TX (US); Jeffrey P. Jones, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/985,789

(22) Filed: Jan. 6, 2011

(65) Prior Publication Data

US 2011/0105816 A1 May 5, 2011

Related U.S. Application Data

(63) Continuation of application No. 11/891,752, filed on Aug. 13, 2007, now Pat. No. 7,893,308.

(60) Provisional application No. 60/840,171, filed on Aug. 25, 2006.

(51) Int. Cl.
*C07C 2/52* (2006.01)
(52) U.S. Cl. ......... 585/403; 585/407; 585/420; 585/418
(58) Field of Classification Search .................. None
See application file for complete search history.

(56) References Cited

U.S. PATENT DOCUMENTS

| | | | |
|---|---|---|---|
| 4,727,206 A | 2/1988 | Clayson et al. | |
| 5,026,937 A | 6/1991 | Bricker | |
| 5,336,825 A | 8/1994 | Choudhary et al. | |
| 5,676,821 A * | 10/1997 | Heyse et al. | 208/135 |
| 5,863,418 A * | 1/1999 | Heyse et al. | 208/135 |
| 6,239,057 B1 | 5/2001 | Ichikawa et al. | |
| 6,426,442 B1 | 7/2002 | Ichikawa et al. | |
| 2002/0179495 A1 * | 12/2002 | Heyse et al. | 208/137 |
| 2004/0147794 A1 | 7/2004 | Brown et al. | |
| 2004/0180975 A1 | 9/2004 | Pan et al. | |
| 2005/0170197 A1 | 8/2005 | Chun et al. | |

FOREIGN PATENT DOCUMENTS

| | | |
|---|---|---|
| EP | 0 546 470 | 6/1993 |
| EP | 1 515 075 | 3/2005 |
| WO | 2004/092060 | 10/2004 |

OTHER PUBLICATIONS

Baker et al., "Alloy Solutions to Metal Dusting Problems in the PetroChemical Industry",Special Metals Corporation, Huntington, West Virginia, publication date not available.
Martinz et al., "Carburization of High Temperature PM-Materials", Materials and Corrosion, 1998, vol. 49, pp. 246-251.
Kempen et al., "The Influence of Metal Dusting on Gas Reactions", Materials and Corrosion, 2004, vol. 55, No. 4, pp. 249-258.
Japan Chemical Week Incorporating Asia Report, "Benzene Synthesized Directly from Methane: Mitsubishi Chem", The Chemical Daily Co., Ltd., vol. 46, No. 2337, ISSN 0047-1755, Oct. 6, 2005.

* cited by examiner

*Primary Examiner* — Tam M Nguyen
(74) *Attorney, Agent, or Firm* — Andrew B. Griffis

(57) ABSTRACT

In a process for converting methane to aromatic hydrocarbons, a feed containing methane is contacted with a dehydrocyclization catalyst in a reaction zone under conditions effective to convert the methane to aromatic hydrocarbons. The reaction zone is contained within a reactor and the reactor or an internal component of the reactor has at least one surface that is chemically exposed to the feed and is formed from a refractory material that exhibits a carbon uptake (mass of carbon absorbed per unit of exposed metal surface area) of less than 25 $g/m^2$ when exposed to mixture of 50 vol % methane and 50 vol % $H_2$ at 900° C. for 168 hours.

19 Claims, 6 Drawing Sheets

PRODUCTION OF AROMATICS FROM METHANE

CROSS REFERENCE TO RELATED APPLICATIONS

This application claims priority from U.S. Provisional Patent Application Ser. No. 60/840,171, filed Aug. 25, 2006, and is a Continuation of application Ser. No. 11/891,752 filed on Aug. 13, 2007, now U.S. Pat. No. 7,893,308, the entire contents of which are incorporated herein by reference.

FIELD

This invention relates to a process for producing aromatic hydrocarbons from methane and, in particular, from natural gas.

BACKGROUND

Aromatic hydrocarbons, particularly benzene, toluene, ethylbenzene and xylenes, are important commodity chemicals in the petrochemical industry. Currently, aromatics are most frequently produced from petroleum-based feedstocks by a variety of processes, including catalytic reforming and catalytic cracking. However, as the world supplies of petroleum feedstocks decrease, there is a growing need to find alternative sources of aromatic hydrocarbons.

One possible alternative source of aromatic hydrocarbons is methane, which is the major constituent of natural gas and biogas. World reserves of natural gas are constantly being upgraded and more natural gas is currently being discovered than oil. Because of the problems associated with transportation of large volumes of natural gas, most of the natural gas produced along with oil, particularly at remote places, is flared and wasted. Hence the conversion of alkanes contained in natural gas directly to higher hydrocarbons, such as aromatics, is an attractive method of upgrading natural gas, providing the attendant technical difficulties can be overcome.

A large majority of the processes currently proposed for converting methane to liquid hydrocarbons involve initial conversion of the methane to synthesis gas, a blend of $H_2$ and CO. However, production of synthesis gas is capital and energy intensive and hence routes that do not require synthesis gas generation are preferred.

A number of alternative processes have been proposed for directly converting methane to higher hydrocarbons. One such process involves catalytic oxidative coupling of methane to olefins followed by the catalytic conversion of the olefins to liquid hydrocarbons, including aromatic hydrocarbons. For example, U.S. Pat. No. 5,336,825 discloses a two-step process for the oxidative conversion of methane to gasoline range hydrocarbons comprising aromatic hydrocarbons. In the first step, methane is converted to ethylene and minor amounts of $C_3$ and $C_4$ olefins in the presence of free oxygen using a rare earth metal promoted alkaline earth metal oxide catalyst at a temperature between 500° C. and 1000° C. The ethylene and higher olefins formed in the first step are then converted to gasoline range liquid hydrocarbons over an acidic solid catalyst containing a high silica pentasil zeolite.

However, oxidative coupling methods suffer from the problems that they involve highly exothermic and potentially hazardous methane combustion reactions and they generate large quantities of environmentally sensitive carbon oxides.

A potentially attractive route for upgrading methane directly into higher hydrocarbons, particularly ethylene, benzene and naphthalene, is dehydroaromatization or reductive coupling. This process typically involves contacting the methane with a catalyst comprising a metal, such as rhenium, tungsten or molybdenum, supported on a zeolite, such as ZSM-5, at high temperature, such as 600° C. to 1000° C. Frequently, the catalytically active species of the metal is the zero valent elemental form or a carbide or oxycarbide.

For example, U.S. Pat. No. 4,727,206 discloses a process for producing liquids rich in aromatic hydrocarbons by contacting methane at a temperature between 600° C. and 800° C. in the absence of oxygen with a catalyst composition comprising an aluminosilicate having a silica to alumina molar ratio of at least 5:1, said aluminosilicate being loaded with (i) gallium or a compound thereof and (ii) a metal or a compound thereof from Group VIIB of the Periodic Table.

In addition, U.S. Pat. No. 5,026,937 discloses a process for the aromatization of methane which comprises the steps of passing a feed stream, which comprises over 0.5 mole % hydrogen and 50 mole % methane, into a reaction zone having at least one bed of solid catalyst comprising ZSM-5, gallium and phosphorus-containing alumina at conversion conditions which include a temperature of 550° C. to 750° C., a pressure less than 10 atmospheres absolute (1000 kPaa) and a gas hourly space velocity of 400 to 7,500 $hr^{-1}$.

Moreover, U.S. Pat. Nos. 6,239,057 and 6,426,442 disclose a process for producing higher carbon number hydrocarbons, e.g., benzene, from low carbon number hydrocarbons, such as methane, by contacting the latter with a catalyst comprising a porous support, such as ZSM-5, which has dispersed thereon rhenium and a promoter metal such as iron, cobalt, vanadium, manganese, molybdenum, tungsten or a mixture thereof. After impregnation of the support with the rhenium and promoter metal, the catalyst is activated by treatment with hydrogen and/or methane at a temperature of about 100° C. to about 800° C. for a time of about 0.5 hr. to about 100 hr. The addition of CO or $CO_2$ to the methane feed is said to increase the yield of benzene and the stability of the catalyst.

However, the successful application of reductive coupling to produce aromatics on a commercial scale requires the solution of a number of serious technical challenges. In particular, the process is highly endothermic, thereby requiring large amounts of heat to be supplied to the reaction. Moreover, the process must be conducted at very high temperatures, typically 800° C. to 1000° C., to ensure reasonable rates of methane conversion. This in turn leads to significant metallurgical challenges in formulating the surfaces of the reactor required to withstand the highest process temperatures and process gases.

Thus, when exposed to hydrocarbons at high temperature, many metals and metal alloys tend to form internal carbides that can cause degradation of their mechanical properties as a result of changes in the local composition of the metal matrix. In addition, carburization can lead to the formation of metastable surface carbides that decompose on subsequent coke deposition and result in the phenomenon of metal dusting, where the surface of the metal disintegrates into powdery carbon and metal particles. The loss of metal results in the formation of pits or holes in the surface of the affected metal component and rapid thinning of the component walls. Moreover, the released metal particles can act as catalysts for the conversion of the hydrocarbon feed into undesirable coke.

Conventional techniques for mitigating carburization in high temperature reactor components include maintaining a protective oxide layer, such as chromium oxide, on the component surfaces by ensuring sufficient oxygen partial pressure in the reactor, typically by the addition of water, and introducing sulfur into the reactor so as to decrease the tendency for metal/hydrocarbon reactions. However, in the reductive coupling of methane to higher hydrocarbons, these approaches are typically unavailable or may have undesirable consequences. The addition of water or other oxygen source to the reactor would tend to convert the methane feed to unwanted carbon oxides, whereas sulfur tends to poison the catalysts generally employed to facilitate reductive coupling reactions and/or downstream conversion steps.

For example, conventional metallurgy used for steam cracking service (e.g., Incoloy® alloy 803) is found to undergo rapid carburization under methane reductive coupling conditions. Alloy 803 has a carbon uptake (grams of carbon absorbed per $m^2$ of exposed surface area) in excess of 80 $g/m^2$ after 168 hours of exposure at 900° C. under 50:50 vol % $CH_4$—$H_2$ mixture, indicating rapid formation of internal carbides. Although the temperature for methane reductive coupling is comparable to steam cracking, it has significantly lower oxygen partial pressure (thereby rendering chromium oxide unstable), leading to rapid carburization of unprotected steam cracking alloy.

In addition to carburization of bulk alloys to form internal carbides, surface reaction of hydrocarbons with metal surfaces and/or reaction of hydrocarbons with metal fines released from alloy surface due to metal dusting can lead to significant coking at exposed metal surfaces under reductive coupling process conditions. Conventional alloys and pure metals (such as nickel, cobalt, and iron) show significant coke formation on metal surfaces after exposure to 50:50 vol % $CH_4$—$H_2$ mixture at 900° C.

An article entitled "Alloy Solutions to Metal Dusting Problems in the Petrochemical Industry" by Baker et al., Special Metals Corporation, Huntington, W. Va. discusses the effect of metal alloy composition on resistance to metal dusting experienced in the steam reforming of methane to produce synthesis gas. The article concludes that nickel based alloys that contain high levels of scale-forming and carbide-forming elements are particularly resistant to corrosion by synthesis gas at temperatures of 400° C. to 800° C.

According to the present invention it has now been found that the problem of carburization of reactor surfaces in reductive coupling reactions can be mitigated by producing the surfaces from a refractory alloy containing at least 2 weight % of at least one of aluminum, magnesium or cerium and/or from a refractory metal or alloy capable of forming a stable, continuous carbide layer under reductive coupling conditions. In addition, it is found that by providing such surfaces with a refractory abrasion-resistant coating, which need not itself be resistant to carbon ingress, the surfaces can be used in reactor internals, such as gas distributors, slide valves and cyclones, that are exposed high velocity gas, moving catalysts particles and other highly erosive environments.

SUMMARY

In one aspect, the present invention resides in a process for converting methane to higher hydrocarbons including aromatic hydrocarbons, the process comprising contacting a feed containing methane with a dehydrocyclization catalyst in a reaction zone under conditions effective to convert said methane to aromatic hydrocarbons, wherein said reaction zone is contained within a reactor and wherein the reactor or an internal component of the reactor has at least one surface that is chemically exposed to said feed and is formed from a refractory material that exhibits a carbon uptake (mass of carbon absorbed per unit of exposed metal surface area) of less than 25 $g/m^2$, preferably 15 $g/m^2$ and most preferably 10 $g/m^2$, when exposed to mixture of 50 vol % methane and 50 vol % $H_2$ at 900° C. for 168 hours.

In a further aspect, the present invention resides in a process for converting methane to higher hydrocarbons including aromatic hydrocarbons, the process comprising contacting a feed containing methane with a dehydrocyclization catalyst in a reaction zone under conditions effective to convert said methane to aromatic hydrocarbons, wherein said reaction zone is contained within a reactor and wherein the reactor or an internal component of the reactor has at least one surface that is chemically exposed to said feed and that is formed from a refractory metal or alloy that comprises, or is capable of forming and/or maintaining under said conditions, a continuous layer of an oxide, carbide, oxycarbide, or mixture thereof stable under said conditions.

In one embodiment, said at least one surface is formed from a refractory alloy containing at least 0.5 weight % of at least one of aluminum, magnesium, yttrium, silicon or cerium.

In another embodiment, said at least one surface is formed from a refractory metal from Groups 4, 5 and 6 of the Periodic Table of the Elements or an alloy thereof, especially molybdenum, tungsten, chromium and/or niobium.

Conveniently, said at least one surface is chemically exposed to said feed through a refractory, abrasion resistant coating, typically comprising at least one of a ceramic, phosphide, nitride, carbide, and oxide.

In yet a further aspect, the present invention resides in a process for converting methane to higher hydrocarbons including aromatic hydrocarbons, the process comprising contacting a feed containing methane with a dehydrocyclization catalyst in a reaction zone under conditions effective to convert said methane to aromatic hydrocarbons, wherein said reaction zone is contained within a reactor and wherein the reactor or an internal component of the reactor has at least one surface that is chemically exposed to said feed and that is formed from a refractory alloy containing at least 0.5 weight % of at least one of aluminum, magnesium, yttrium, silicon or cerium.

In one embodiment, said at least one surface is formed from an iron-based alloy. Conveniently, said iron-based alloy comprises chromium, such as between about 15 and about 49 weight % chromium, and at least 2 weight %, such as between about 4 and about 6 weight %, aluminum in addition to iron.

In another embodiment, said at least one surface is formed from a nickel-based alloy. Conveniently, said nickel-based alloy comprises chromium, such as between about 15 and about 49 weight % chromium, and at least 2 weight %, such as between about 3 and about 5 weight %, aluminum in addition to nickel.

In yet another embodiment, said at least one surface is formed from a cobalt-based alloy. Conveniently, said cobalt-based alloy comprises chromium, such as between about 15 and about 49 weight % chromium, and at least 2 weight %, such as between about 3 and about 5 weight %, aluminum in addition to cobalt.

DETAILED DESCRIPTION OF THE EMBODIMENTS

Figure 1:
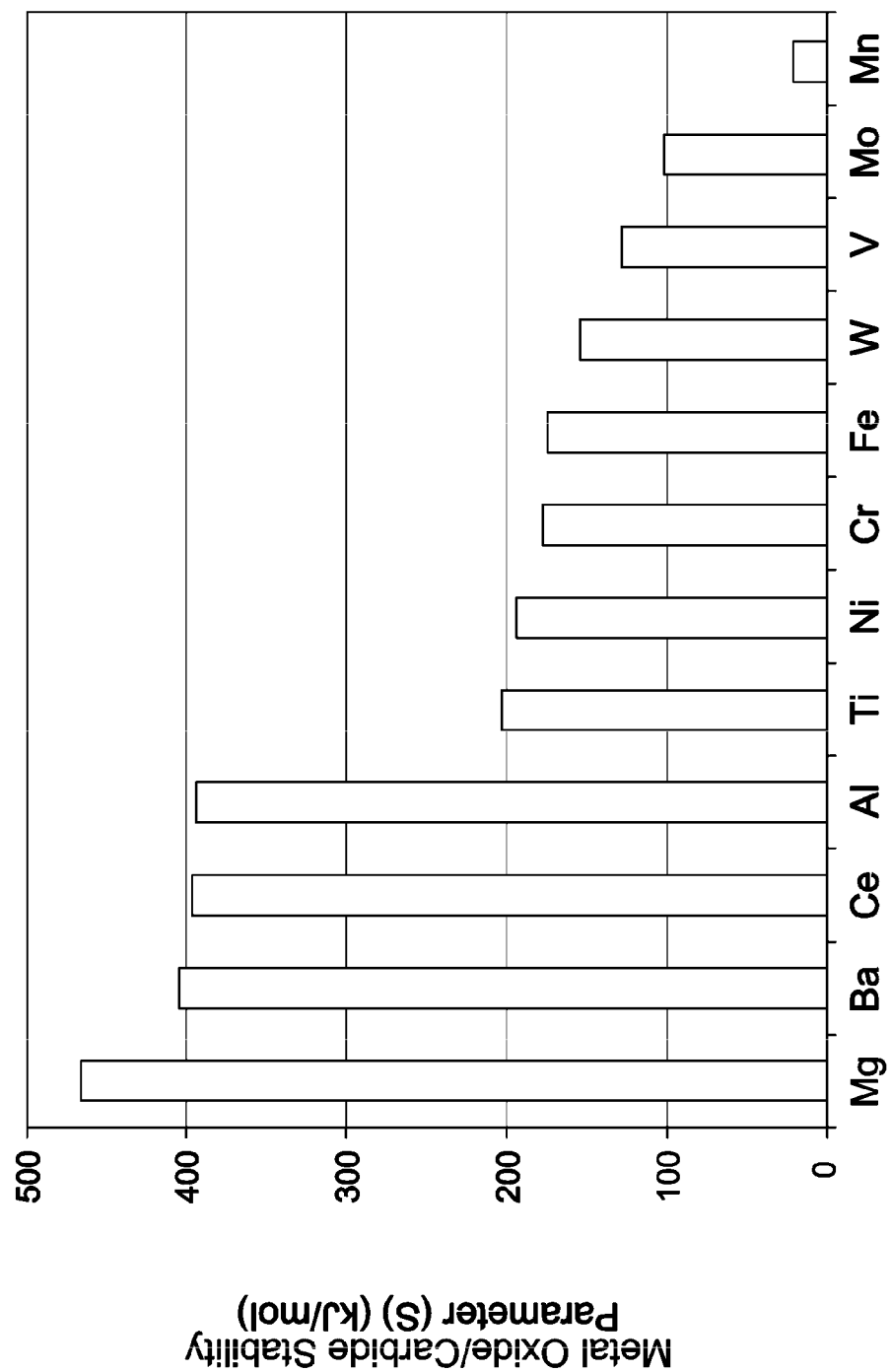
FIG. 1 is a bar graph showing the calculated metal oxide/carbide stability parameter for various metals.

As used herein each of the terms "iron-based alloy", "nickel-based alloy" and "cobalt-based alloy" means an alloy containing greater than 50 weight % of iron, nickel and cobalt respectively.

References herein to the Periodic Table of the Elements employ the new numbering scheme for the Periodic Table Groups as disclosed in Chemical and Engineering News, 63(5), 27 (1985).

The present invention provides a process for producing aromatic hydrocarbons by contacting a feedstock containing methane, typically together with $H_2$, CO and/or $CO_2$, with a dehydrocyclization catalyst in a reaction zone under conditions effective to convert the methane to aromatic hydrocarbons and hydrogen. According to the invention, the reaction zone is contained within a reactor and the reactor or an internal component of the reactor has at least one surface that is chemically exposed to said feed and that is formed from a refractory material that exhibits a carbon uptake (mass of carbon absorbed per unit of exposed metal surface area) of less than 25 g/m², preferably 15 g/m² and most preferably 10 g/m², when exposed to mixture of 50 vol % methane and 50 vol % $H_2$ at 900° C. for 168 hours. Typically, said least one surface is formed from a refractory metal or alloy that comprises, or is capable of forming and/or maintaining under said conditions, a continuous layer of an oxide, carbide, oxycarbide, or mixture thereof stable under said conditions.

The present invention has identified refractory materials that are resistant to carburization when contacted with feedstock containing methane for producing aromatic hydrocarbons at high temperatures. These refractory materials, which may be directly exposed to process gases and conditions, can be used as bulk metal alloys or as cladding to conventional alloys where the carburization resistance of the conventional alloys is improved due to the high carburization resistance of its surface cladding. Examples of reactor internal components that would typically be provided with the present carburization resistant surface include gas distributors, grids, slide valves, gratings, structured packings and shrouds.

When the surface of a metal alloy is exposed to hydrocarbon gases at high temperatures, the metal surface is able to catalyze the conversion of hydrocarbons to coke leading to significant coke build-up. The present invention has identified carbide-forming metals (such as, molybdenum, tungsten, etc.) that are resistant to surface coking due to the formation of a metal carbide surface layer under reductive coupling conditions. These carbide-forming metals can be used as bulk metallurgy or as surface coatings or as cladding to conventional alloys to provide improved coking/carburization resistance.

Where the surface will be exposed to erosive environments, such as high velocity gases and/or moving catalysts particles, it may be desirable to provide the surface with a refractory, abrasion resistant coating, typically comprising at least one of a ceramic, phosphide, nitride, carbide, and oxide. This is because exposure of the alloy surface to high velocity gases and/or moving catalyst particles can erode the protective metal oxide or carbide layer present on its surface, which may lead to increased rate of carburization of the bulk alloy. Moreover, surface erosion can preferentially deplete the metal alloy of its constituent metal that forms the protective layer (such as aluminum), thereby making it harder to repair defects in the surface protective oxide/carbide layer under process conditions. In addition to mitigating surface erosion, these abrasion-resistant coatings can serve as thermal insulators which, in some applications, can lower surface alloy temperatures when used in conjunction with cooling systems. Since the underlying surface is resistant to carburization, there is no requirement that the abrasive coating is also resistant to carbon ingress. Examples of reactor surfaces that are desirably provided with abrasion resistant coatings are the operating surfaces of reactor internals, such as gas distributors, slide valves and cyclones.

Feedstock

Any methane-containing feedstock can be used in the process of the invention but in general the present process is intended for use with a natural gas feedstock. Other suitable methane-containing feedstocks include those obtained from sources such as coal beds, landfills, agricultural or municipal waste fermentation, and/or refinery gas streams.

Methane-containing feedstocks, such as natural gas, typically contain carbon dioxide and ethane in addition to methane. Ethane and other aliphatic hydrocarbons that may be present in the feed can of course be converted to desired aromatics products in the dehydrocyclization step. In addition, as will be discussed below, carbon dioxide can also be converted to useful aromatics products either directly in the dehydrocyclization step or indirectly through conversion to methane and/or ethane in the hydrogen rejection step.

Nitrogen and/or sulfur impurities are also typically present in methane-containing streams may be removed, or reduced to low levels, prior to use of the streams in the process of the invention. In an embodiment, the feed to the dehydrocyclization step contains less than 100 ppm, for example less than 10 ppm, such as less than 1 ppm each of nitrogen and sulfur compounds.

In addition to methane, the feed to the dehydrocyclization step may contain at least one of hydrogen, water, carbon monoxide and carbon dioxide in order to assist in coke mitigation. These additives can be introduced as separate co-feeds or can be present in the methane stream, such as, for example, where the methane stream is derived from natural gas containing carbon dioxide. Other sources of carbon dioxide may include flue gases, LNG plants, hydrogen plants, ammonia plants, glycol plants and phthalic anhydride plants.

In one embodiment, the feed to the dehydrocyclization step contains carbon dioxide and comprises about 90 to about 99.9 mol %, such as about 97 to about 99 mol %, methane and about 0.1 to about 10 mol %, such as about 1 to about 3 mol %, $CO_2$. In another embodiment, the feed to the dehydrocyclization step contains carbon monoxide and comprises about 80 to about 99.9 mol %, such as about 94 to about 99 mol %, methane and about 0.1 to about 20 mol %, such as about 1 to about 6 mol %, CO. In a further embodiment, the feed to the dehydrocyclization step contains steam and comprises about 90 to about 99.9 mol %, such as about 97 to about 99 mol %, methane and about 0.1 to about 10 mol %, such as about 1 to about 5 mol %, steam. In yet a further embodiment, the feed to the dehydrocyclization step contains hydrogen and comprises about 80 to about 99.9 mol %, such as about 95 to about 99 mol %, methane and about 0.1 to about 20 mol %, such as about 1 to about 5 mol %, hydrogen.

The feed to the dehydrocyclization step can also contain higher hydrocarbons than methane, including aromatic hydrocarbons. Such higher hydrocarbons can be recycled from the hydrogen rejection step, added as separate co-feeds or can be present in the methane stream, such as, for example, when ethane is present in a natural gas feed. Higher hydrocarbons recycled from the hydrogen rejection step typically include one-ring aromatics and/or paraffins and olefins having predominately 6 or less, such as 5 or less, for example 4 or less, typically 3 or less carbon atoms. In general, the feed to the dehydrocyclization step contains less than 5 wt %, such as less than 3 wt %, of $C_3+$hydrocarbons.

Dehydrocyclization

In the dehydrocyclization step of the present process, the methane containing feedstock is contacted with a dehydrocyclization catalyst under conditions, normally non-oxidizing conditions and preferably reducing conditions, effective to convert the methane to higher hydrocarbons, including benzene and naphthalene. The principal net reactions involved are as follows:

$$2CH_4 \leftrightarrow C_2H_4+2H_2 \quad \text{(Reaction 1)}$$

$$6CH_4 \leftrightarrow C_6H_6+9H_2 \quad \text{(Reaction 2)}$$

$$10CH_4 \leftrightarrow C_{10}H_8+16H_2 \quad \text{(Reaction 3)}$$

Carbon monoxide and/or dioxide that may be present in the feed improves catalyst activity and stability by facilitating reactions such as:

$$CO_2+coke \rightarrow 2CO \quad \text{(Reaction 4)}$$

but negatively impacts equilibrium by allowing competing net reactions, such as;

$$CO_2+CH_4 \leftrightarrow CO+2H_2 \quad \text{(Reaction 5)}.$$

Suitable conditions for the dehydrocyclization step include a temperature of about 400° C. to about 1200° C., such as about 500° C. to about 1000° C., for example about 600° C. to about 1000° C., especially about 800° C. to about 950° C., a pressure of about 1 kPa to about 1000 kPa, such as about 30 to about 700 kPa, for example about 50 kPa to about 200 kPa and a weight hourly space velocity of about 0.01 to about 1000 $hr^{-1}$, such as about 0.1 to about 500 $hr^{-1}$, for example about 1 to about 20 $hr^{-1}$. Conveniently, the dehydrocyclization step is conducted in the absence of $O_2$.

Any dehydrocyclization catalyst effective to convert methane to aromatics can be used in the present process, although generally the catalyst will include a metal component, particularly a transition metal or compound thereof, on an inorganic support. Conveniently, the metal component is present in an amount between about 0.1% and about 20%, such as between about 1% and about 10%, by weight of the total catalyst. Generally, the metal will be present in the catalyst in elemental form or as a carbide species.

Suitable metal components for the catalyst include calcium, magnesium, barium, yttrium, lanthanum, scandium, cerium, titanium, zirconium, hafnium, vanadium, niobium, tantalum, chromium, molybdenum, tungsten, manganese, rhenium, iron, ruthenium, cobalt, rhodium, iridium, nickel, palladium, copper, silver, gold, zinc, aluminum, gallium, silicon, germanium, indium, tin, lead, bismuth and transuranium metals. Such metal components may be present in elemental form or as metal compounds, such as oxides, carbides, nitrides and/or phosphides, and may be employed alone or in combination. Platinum and osmium can also be used as one of the metal component but, in general, are not preferred.

The inorganic support may be either amorphous or crystalline and in particular may be an oxide, carbide or nitride of boron, aluminum, silicon, phosphorous, titanium, scandium, chromium, vanadium, magnesium, manganese, iron, zinc, gallium, germanium, yttrium, zirconium, niobium, molybdenum, indium, tin, barium, lanthanum, hafnium, cerium, tantalum, tungsten, or other transuranium elements. In addition, the support may be a porous material, such as a microporous crystalline material or a mesoporous material. As used herein the term "microporous" refers to pores having a diameter of less than 2 nanometers, whereas the term "mesoporous" refers to pores having a diameter of from 2 to 50 nanometers.

Suitable microporous crystalline materials include silicates, aluminosilicates, titanosilicates, aluminophosphates, metallophosphates, silicoaluminophosphates or their mixtures. Such microporous crystalline materials include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49 and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y and dealuminized Y), LTL (e.g., zeolite L), IWW (e.g., ITQ-22), VFI (e.g., VPI-5), AEL (e.g., SAPO-11), AFI (e.g., ALPO-5) and AFO (SAPO-41), as well as materials such as MCM-68, EMM-1, EMM-2, ITQ-23, ITQ-24, ITQ-25, ITQ-26, ETS-2, ETS-10, SAPO-17, SAPO-34 and SAPO-35. Suitable mesoporous materials include MCM-41, MCM-48, MCM-50, FSM-16 and SBA-15.

Examples of preferred catalysts include molybdenum, tungsten, zinc, rhenium and compounds and combinations thereof on ZSM-5, silica or alumina.

The metal component can be dispersed on the inorganic support by any means well known in the art such as co-precipitation, incipient wetness, evaporation, impregnation, spray-drying, sol-gel, ion-exchange, chemical vapor deposition, diffusion and physical mixing. In addition, the inorganic support can be modified by known methods, such as, for example, steaming, acid washing, caustic washing and/or treatment with silicon-containing compounds, phosphorus-containing compounds, and/or elements or compounds of Groups 1, 2, 3 and 13 of the Periodic Table of Elements. Such modifications can be used to alter the surface activity of the support and hinder or enhance access to any internal pore structure of the support.

The dehydrocyclization step is conducted by contacting the methane-containing feedstock with the dehydrocyclization catalyst in one or more fixed bed, moving bed or fluidized bed reaction zones. Generally, the feedstock is contacted in the or each reaction zone with a moving bed of dehydrocyclization catalyst, wherein the feedstock flows countercurrent to the direction of movement of the dehydrocyclization catalyst. In one embodiment, the reaction zone comprises a settling bed reactor, by which is meant a vertically disposed reactor in which particulate catalyst enters at or near the top of the reactor and flows under gravity to form a catalyst bed, while the feed enters the reactor at or near the base of the reactor and flows upwardly through the catalyst bed. In an alternative embodiment, the reaction zone comprises a plurality of series-connected fluidized bed reactors in which particulate catalyst is cascaded in one direction from one reactor to the next adjacent reactor in the series, while the feed is passed through and between the reactors in the opposite direction.

Not only is the dehydrocyclization reaction conducted at high temperature, but also the materials present in the reaction zone, methane from the feed and higher hydrocarbons in the product, mean that the atmosphere is highly carburizing. Extensive experimentation has shown that conventional refractory alloys, such as Incoloy® alloy 803, used in other high temperature environments, such as steam cracking, undergo rapid degradation when exposed to the highly carburizing atmosphere of a dehydrocyclization reaction. In particular, it has now been found that the surfaces that are chemically exposed to the high temperature carburizing atmosphere present in the dehydrocyclization reaction zone should be formed from a refractory material that exhibits a carbon uptake (mass of carbon absorbed per unit of exposed metal surface area) of less than 25 g/m$^2$, preferably 15 g/m$^2$ and most preferably 10 g/m$^2$, when exposed to mixture of 50 vol % methane and 50 vol % $H_2$ at 900° C. for 168 hours.

Suitable materials with the required low level of carbon uptake include refractory metals and refractory alloys that comprise, or are capable of forming and/or maintaining in-situ during the dehydrocyclization reaction, a continuous surface oxide or carbide layer that is stable under the dehydrocyclization conditions.

It is to be appreciated that the required surface oxide layer can be produced during the dehydrocyclization reaction when the methane feed contains water, carbon monoxide and/or carbon dioxide in order to assist in coke mitigation. Alternatively, the surface oxide layer can be produced by pre-oxidizing the surface before the surface is exposed to the dehydrocyclization conditions, either by effecting the pre-oxidation in situ in the reaction zone or by pre-oxidizing the alloy stock used to fabricate the relevant surfaces of the reaction zone. This is conveniently achieved by exposing the surface to a water-containing atmosphere, preferably 5% water in hydrogen, at a temperature of about 700° C. to about 1100° C. for a time of about 6 hours to about 48 hours.

Materials capable of forming a stable carbide layer in-situ during the dehydrocyclization reaction include all of the refractory metal elements listed in Groups 4, 5 and 6 of the Periodic Table of the Periodic Table (e.g. Ti, Zr, Hf, V, Nb, Ta, Cr, Mo, W) and their alloys. For instance, suitable niobium alloys could include Nb—Ti alloys, C103 (Nb with 10 wt % Hf and 1 wt % Ti) alloy and Nb-1 wt % Zr alloy. In addition, there are many titanium alloys that have been developed for aerospace applications and should be suitable (e.g. Ti64, IMI-550, Ti-811, Ti6246). Preferred materials include molybdenum, tungsten, chromium and niobium.

Refractory alloys capable of forming and/or maintaining a stable oxide layer in-situ during the dehydrocyclization reaction include alloys containing at least 0.5 weight %, such as at least 2 weight %, of at least one of aluminum, magnesium, yttrium, silicon or cerium.

In one embodiment, the alloy is an iron-based alloy, that is an alloy containing greater than 50 weight % of iron. Conveniently, the iron-based alloy comprises at least 0.5 weight %, such as at least 2 weight %, up to about 35 weight %, such as between about 4 and about 6 weight %, aluminum and preferably contains chromium, such as between about 15 and about 49 weight % chromium, in addition to the iron. Examples of suitable iron-based alloys include Kanthal® APM (composed of 72 weight % iron, 22 weight % chromium and 5.8 weight % aluminum), Incoloy® MA956 (composed of 74 weight % iron, 20 weight % chromium, 4.75 weight % aluminum and 0.5 weight % nickel) and ODS alloy PM2000 (composed of 74 weight % iron, 20 weight % chromium, 5.5 weight % aluminum and 0.5 weight % yttrium).

In another embodiment, the alloy is a nickel-based alloy, that is an alloy containing greater than 50 weight % of nickel. Conveniently, the nickel-based alloy comprises at least 0.5 weight %, such as at least 2 weight % up to about 35 weight %, such as between about 3 and about 5 weight % aluminum and preferably contains chromium, such as between about 15 and about 49 weight % chromium, in addition to the nickel. Examples of suitable nickel-based alloys include Haynes® alloy 214 (composed of 75 weight % nickel, 16 weight % chromium, 4.75 weight % aluminum and 3 weight % iron) and Inconel® alloy 693 (composed of 62 weight % nickel, 29 weight % chromium, 4 weight % iron and 3.1 weight % aluminum).

In yet another embodiment, the alloy is a cobalt-based alloy, that is an alloy containing greater than 50 weight % of cobalt. Conveniently, the cobalt-based alloy comprises at least 0.5 weight %, such as at least 2 weight % up to about 35 weight %, such as between about 3 and about 5 weight % aluminum and preferably contains chromium, such as between about 15 and about 49 weight % chromium, in addition to the cobalt. Example of suitable cobalt-based alloy includes a sub-class of MCrAlY type coatings, wherein M (which can be nickel, iron and/or cobalt) is cobalt, Cr is chromium up to 35 weight %, Al is aluminum up to 15 wt % and Y is yttrium up to 1 weight %.

Refractory alloys capable of forming and/or maintaining a stable oxide layer either prior to, or during, the dehydrocyclization reaction include Haynes® alloy 214 and Kanthal® APMT.

The major components of the effluent from the dehydrocyclization step are hydrogen, benzene, naphthalene, carbon monoxide, ethylene, and unreacted methane. Typically, the effluent contains at least 5 wt %, such as at least 10 wt %, for example at least 20 wt %, preferably at least 30 wt %, more aromatic rings than the feed.

The benzene and naphthalene are then recovered from the dehydrocyclization effluent, for example, by solvent extraction followed by fractionation. However, as will be discussed below, at least part of these aromatic components can be submitted to an alkylation step, before or after product recovery, to produce higher value materials, such as xylenes.

Hydrogen Management

Since hydrogen is a major component of the dehydrocyclization effluent, after recovery of the aromatic products, the effluent is subjected to a hydrogen rejection step to reduce the hydrogen content of the effluent before the unreacted methane is recycled to the dehydrocyclization step and to maximize feed utilization. Typically the hydrogen rejection step comprises reacting at least part of the hydrogen in the dehydrocyclization effluent with an oxygen-containing species, preferably CO and/or $CO_2$, to produce water and a second effluent stream having a reduced hydrogen content compared with the first (dehydrocyclization) effluent stream.

Conveniently, the hydrogen rejection step includes (i) methanation and/or ethanation, (ii) a Fischer-Tropsch process, (iii) synthesis of $C_1$ to $C_3$ alcohols, particularly methanol, and other oxygenates, (iv) synthesis of light olefins, paraffins and/or aromatics by way of a methanol or dimethyl ether intermediate and/or (v) selective hydrogen combustion. These steps may be employed sequentially to gain the greatest benefit; for example Fischer-Tropsch may first be employed to yield a $C_2$+ enriched stream followed by methanation to achieve high conversion of the $H_2$.

Typically, as described below, the hydrogen rejection step will generate hydrocarbons, in which case, after separation of the co-produced water, at least portion of the hydrocarbons are conveniently recycled to the dehydrocyclization step. For example, where the hydrocarbons produced in the hydrogen rejection step comprise paraffins and olefins, the portion recycled to the dehydrocyclization step conveniently comprises paraffins or olefins with 6 or less carbon atoms, such as 5 or less carbon atoms, for example 4 or less carbon atoms or 3 or less carbon atoms. Where, the hydrocarbons produced in the hydrogen rejection step comprise aromatics, the portion recycled to the dehydrocyclization step conveniently comprises single ring aromatic species.

Methanation/Ethanation

In one embodiment the hydrogen rejection step comprises reaction of at least part of the hydrogen in the dehydrocyclization effluent with carbon dioxide to produce methane and/or ethane according to the following net reactions:

$$CO_2 + 4H_2 \leftrightarrow CH_4 + 2H_2O \quad \text{(Reaction 6)}$$

$$2CO_2 + 7H_2 \leftrightarrow C_2H_6 + 4H_2O \quad \text{(Reaction 7)}$$

The carbon dioxide employed is conveniently part of a natural gas stream and preferably the same natural gas stream used as the feed to the dehydrocyclization step. Where the carbon dioxide is part of a methane-containing stream, the $CO_2:CH_4$ of the stream is conveniently maintained between about 1:1 and about 0.1:1. Mixing of the carbon dioxide-containing stream and the dehydrocyclization effluent is conveniently achieved by supplying the gaseous feeds to the inlet of a jet ejector.

The hydrogen rejection step to produce methane or ethane normally employs a $H_2:CO_2$ molar ratio close to the stoichiometric proportions required for the desired Reaction 6 or Reaction 7, although small variations can be made in the stoichiometric ratio if it is desired to produce a $CO_2$-containing or $H_2$-containing second effluent stream. The hydrogen rejection step to produce methane or ethane is conveniently effected in the presence of a bifunctional catalyst comprising a metal component, particularly a transition metal or compound thereof, on an inorganic support. Suitable metal components comprise copper, iron, vanadium, chromium, zinc, gallium, nickel, cobalt, molybdenum, ruthenium, rhodium, palladium, silver, rhenium, tungsten, iridium, platinum, gold, gallium and combinations and compounds thereof. The inorganic support may be an amorphous material, such as silica, alumina or silica-alumina, or like those listed for the dehydroaromatization catalyst. In addition, the inorganic support may be a crystalline material, such as a microporous or mesoporous crystalline material. Suitable porous crystalline materials include the aluminosilicates, aluminophosphates and silicoaluminophosphates listed above for the dehydrocyclization catalyst.

The hydrogen rejection step to produce methane and/or ethane can be conducted over a wide range of conditions including a temperature of about 100° C. to about 900° C., such as about 150° C. to about 500° C., for example about 200° C. to about 400° C., a pressure of about 200 kPa to about 20,000 kPa, such as about 500 to about 5000 kPa and a weight hourly space velocity of about 0.1 to about 10,000 hr$^{-1}$, such as about 1 to about 1,000 hr$^{-1}$. $CO_2$ conversion levels are typically between 20 and 100% and preferably greater than 90%, such as greater than 99%. This exothermic reaction may be carried out in multiple catalyst beds with heat removal between beds. In addition, the lead bed(s) may be operated at higher temperatures to maximize kinetic rates and the tail beds(s) may be operated at lower temperatures to maximize thermodynamic conversion.

The main products of the reaction are water and, depending on the $H_2:CO_2$ molar ratio, methane, ethane and higher alkanes, together with some unsaturated $C_2$ and higher hydrocarbons. In addition, some partial hydrogenation of the carbon dioxide to carbon monoxide is preferred. After removal of the water, the methane, carbon monoxide, any unreacted carbon dioxide and higher hydrocarbons can be fed directly to the dehydrocyclization step to generate additional aromatic products.

Fischer-Tropsch Process

In another embodiment the hydrogen rejection step comprises reaction of at least part of the hydrogen in the dehydrocyclization effluent with carbon monoxide according to the Fischer-Tropsch process to produce $C_2$ to $C_5$ paraffins and olefins.

The Fischer-Tropsch process is well known in the art, see for example, U.S. Pat. Nos. 5,348,982 and 5,545,674 incorporated herein by reference. The process typically involves the reaction of hydrogen and carbon monoxide in a molar ratio of about 0.5:1 to about 4:1, preferably about 1.5:1 to about 2.5:1, at a temperature of about 175° C. to about 400° C., preferably about 180° C. to about 240° C. and a pressure of about 1 to about 100 bar (100 to 10,000 kPa), preferably about 10 to about 40 bar (1,000 to 4,000 kPa), in the presence of a Fischer-Tropsch catalyst, generally a supported or unsupported Groups 8-10, non-noble metal, e.g., Fe, Ni, Ru, Co, with or without a promoter, e.g. ruthenium, rhenium, hafnium, zirconium, titanium. Supports, when used, can be refractory metal oxides such as Groups 4 and 14, i.e., titania, zirconia, or silica, alumina, or silica-alumina. In one embodiment, the catalyst comprises a non-shifting catalyst, e.g., cobalt or ruthenium, preferably cobalt, with rhenium or zirconium as a promoter, preferably cobalt and rhenium supported on silica or titania, preferably titania.

In another embodiment, the hydrocarbon synthesis catalyst comprises a metal, such as Cu, Cu/Zn or Cr/Zn, on the ZSM-5 and the process is operated to generate significant quantities of single-ring aromatic hydrocarbons. An example of such a process is described in *Study of Physical Mixtures of $Cr_2O_3$—ZnO and ZSM-5 Catalysts for the Transformation of Syngas into Liquid Hydrocarbons* by Jose Erena; Ind. Eng. Chem. Res. 1998, 37, 1211-1219, incorporated herein by reference.

The Fischer-Tropsch liquids, i.e., $C_5^+$, are recovered and light gases, e.g., unreacted hydrogen and CO, $C_1$ to $C_3$ or $C_4$ and water are separated from the heavier hydrocarbons. The heavier hydrocarbons can then be recovered as products or fed to the dehydrocyclization step to generate additional aromatic products.

The carbon monoxide required for the Fischer-Tropsch reaction can be provided wholly or partly by the carbon monoxide present in or cofed with the methane-containing feed and generated as a by-product in the dehydrocyclization step. If required, additional carbon monoxide can be generated by feeding carbon dioxide contained, for example, in natural gas, to a shift catalyst whereby carbon monoxide is produced by the reverse water gas shift reaction:

$$CO_2 + H_2 \leftrightarrow CO + H_2O \quad \text{(Reaction 8)}$$

and by the following reaction:

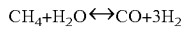

$$CH_4 + H_2O \leftrightarrow CO + 3H_2$$

Alcohol Synthesis

In a further embodiment the hydrogen rejection step comprises reaction of at least part of the hydrogen in the dehydrocyclization effluent with carbon monoxide to produce $C_1$ to $C_3$ alcohols, and particularly methanol. The production of methanol and other oxygenates from synthesis gas is also well-known and is described in, for example, in U.S. Pat. Nos. 6,114,279; 6,054,497; 5,767,039; 5,045,520; 5,254,520; 5,610,202; 4,666,945; 4,455,394; 4,565,803; 5,385,949, the descriptions of which are incorporated herein by reference. Typically, the synthesis gas employed has a molar ratio of hydrogen ($H_2$) to carbon oxides ($CO+CO_2$) in the range of from about 0.5:1 to about 20:1, preferably in the range of from about 2:1 to about 10:1, with carbon dioxide optionally being present in an amount of not greater than 50% by weight, based on total weight of the syngas.

The catalyst used in the methanol synthesis process generally includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide, optionally in the presence of an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

The methanol synthesis process can be conducted over a wide range of temperatures and pressures. Suitable temperatures are in the range of from about 150° C. to about 450° C., such as from about 175° C. to about 350° C., for example from about 200° C. to about 300° C. Suitable pressures are in the range of from about 1,500 kPa to about 12,500 kPa, such as from about 2,000 kPa to about 10,000 kPa, for example 2,500 kPa to about 7,500 kPa. Gas hourly space velocities vary depending upon the type of process that is used, but generally the gas hourly space velocity of flow of gas through the catalyst bed is in the range of from about 50 $hr^{-1}$ to about 50,000 $hr^{-1}$, such as from about 250 $hr^{-1}$ to about 25,000 $hr^{-1}$, more preferably from about 500 $hr^{-1}$ to about 10,000 $hr^{-1}$. This exothermic reaction may be carried out in either fixed or fluidized beds, including multiple catalyst beds with heat removal between beds. In addition, the lead bed(s) may be operated at higher temperatures to maximize kinetic rates and the tail beds(s) may be operated at lower temperatures to maximize thermodynamic conversion.

The resultant methanol and/or other oxygenates can be sold as a separate product, can be used to alkylate the aromatics generated in the dehydrocyclization step to higher value products, such as xylenes, or can be used as a feedstock for the production of lower olefins, particularly ethylene and propylene. The conversion of methanol to olefins is a well-known process and is, for example, described in U.S. Pat. No. 4,499,327, incorporated herein by reference.

Selective Hydrogen Combustion

In yet another embodiment, the hydrogen rejection step comprises selective hydrogen combustion, which is a process in which hydrogen in a mixed stream is reacted with oxygen to form water or steam without substantially reacting hydrocarbons in the stream with oxygen to form carbon monoxide, carbon dioxide, and/or oxygenated hydrocarbons. Generally, selective hydrogen combustion is carried out in the presence of an oxygen-containing solid material, such as a mixed metal oxide, that will release a portion of the bound oxygen to the hydrogen.

One suitable selective hydrogen combustion process is described in U.S. Pat. No. 5,430,210, incorporated herein by reference, and comprises contacting at reactive conditions a first stream comprising hydrocarbon and hydrogen and a second stream comprising oxygen with separate surfaces of a membrane impervious to non-oxygen containing gases, wherein said membrane comprises a metal oxide selective for hydrogen combustion, and recovering selective hydrogen combustion product. The metal oxide is typically a mixed metal oxide of bismuth, indium, antimony, thallium and/or zinc.

U.S. Pat. No. 5,527,979, incorporated herein by reference, describes a process for the net catalytic oxidative dehydrogenation of alkanes to produce alkenes. The process involves simultaneous equilibrium dehydrogenation of alkanes to alkenes and the selective combustion of the hydrogen formed to drive the equilibrium dehydrogenation reaction further to the product alkenes. In particular, the alkane feed is dehydrogenated over an equilibrium dehydrogenation catalyst in a first reactor, and the effluent from the first reactor, along with oxygen, is then passed into a second reactor containing a metal oxide catalyst which serves to selectively catalyze the combustion of hydrogen. The equilibrium dehydrogenation catalyst may comprise platinum and the selective metal oxide combustion catalyst may contain bismuth, antimony, indium, zinc, thallium, lead and tellurium or a mixture thereof.

U.S. Patent Application Publication No. 2004/0152586, published Aug. 5, 2004 and incorporated herein by reference, describes a process for reducing the hydrogen content of the effluent from a cracking reactor. The process employs a catalyst system comprising (1) at least one solid acid cracking component and (2) at least one metal-based selective hydrogen combustion component consisting essentially of (a) a metal combination selected from the group consisting of:

i) at least one metal from Group 3 and at least one metal from Groups 4-15 of the Periodic Table of the Elements;
 ii) at least one metal from Groups 5-15 of the Periodic Table of the Elements, and at least one metal from at least one of Groups 1, 2, and 4 of the Periodic Table of the Elements;
 iii) at least one metal from Groups 1-2, at least one metal from Group 3, and at least one metal from Groups 4-15 of the Periodic Table of the Elements; and
 iv) two or more metals from Groups 4-15 of the Periodic Table of the Elements and (b) at least one of oxygen and sulfur, wherein the at least one of oxygen and sulfur is chemically bound both within and between the metals.

The selective hydrogen combustion reaction of the present invention is generally conducted at a temperature in the range of from about 300° C. to about 850° C. and a pressure in the range of from about 1 atm to about 20 atm (100 to 2000 kPa).

Aromatic Product Recovery/Treatment

The major products of the dehydrocyclization step are benzene and naphthalene. These products can be separated from the dehydrocyclization effluent, typically by solvent extraction followed by fractionation, and then sold directly as commodity chemicals. Alternatively, some or all of the benzene and/or naphthalene can be alkylated to produce, for example, toluene, xylenes and alkyl naphthalenes and/or can be subjected to hydrogenation to produce, for example, cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin).

Aromatics Alkylation

Alkylation of aromatic compounds such as benzene and naphthalene is well known in the art and typically involves reaction of an olefin, alcohol or alkyl halide with the aromatic species in the gas or liquid phase in the presence of an acid catalyst. Suitable acid catalysts include medium pore zeolites (i.e., those having a Constraint Index of 2-12 as defined in U.S. Pat. No. 4,016,218), including materials having the framework types MFI (e.g., ZSM-5 and silicalite), MEL (e.g., ZSM-11), MTW (e.g., ZSM-12), TON (e.g., ZSM-22), MTT (e.g., ZSM-23), MFS (e.g., ZSM-57) and FER (e.g., ZSM-35) and ZSM-48, as well as large pore zeolites (i.e., those having a Constraint Index of less than 2) such as materials having the framework types BEA (e.g., zeolite beta), FAU (e.g., ZSM-3, ZSM-20, zeolites X, Y, ultrastabilized Y and dealuminized Y), MOR (e.g., mordenite), MAZ (e.g., ZSM-4), MEI (e.g., ZSM-18) and MWW (e.g., MCM-22, PSH-3, SSZ-25, ERB-1, ITQ-1, ITQ-2, MCM-36, MCM-49 and MCM-56).

In one embodiment of the present process, benzene is recovered from the dehydrocyclization effluent and then alkylated with an olefin, such as ethylene produced as a by-product of a hydrogen rejection step employing ethanation/methanation. Typical conditions for carrying out the vapor phase alkylation of benzene with ethylene include a temperature of from about 650 to 900° F. (343 to 482° C.), a pressure of about atmospheric to about 3000 psig (100 to 20,800 kPa), a WHSV based on ethylene of from about 0.5 to about 2.0 $hr^{-1}$ and a mole ratio of benzene to ethylene of from 1:1 to 30:1. Liquid phase alkylation of benzene with ethylene may be carried out at a temperature between 300 and 650° F. (150 to 340° C.), a pressure up to about 3000 psig (20,800 kPa), a WHSV based on ethylene of from about 0.1 to about 20 $hr^{-1}$ and a mole ratio of benzene to ethylene of from 1:1 to 30:1.

Preferably, the benzene ethylation is conducted under at least partial liquid phase conditions using a catalyst comprising at least one of zeolite beta, zeolite Y, MCM-22, PSH-3, SSZ-25, ERB-1, ITQ-1, ITQ-2, ITQ-13, ZSM-5 MCM-36, MCM-49 and MCM-56.

The benzene ethylation can be conducted at the site of the dehydrocyclization/hydrogen rejection process or the benzene can be shipped to another location for conversion to ethylbenzene. The resultant ethylbenzene can then be sold, used as a precursor in, for example, the production of styrene or isomerized by methods well known in the art to mixed xylenes.

In another embodiment of the present process, the alkylating agent is methanol or dimethylether (DME) and is used to alkylate benzene and/or naphthalene recovered from the dehydrocyclization effluent to produce toluene, xylenes, methylnaphthalenes and/or dimethylnaphthalenes. Where the methanol or DME is used to alkylate benzene, this is conveniently effected in presence of catalyst comprising a zeolite, such as ZSM-5, zeolite beta, ITQ-13, MCM-22, MCM-49, ZSM-11, ZSM-12, ZSM-22, ZSM-23, ZSM-35, and ZSM-48, which has been modified by steaming so as to have a Diffusion Parameter for 2,2 dimethylbutane of about 0.1-15 $sec^{-1}$ when measured at a temperature of 120° C. and a 2,2 dimethylbutane pressure of 60 torr (8 kPa). Such a process is selective to the production of para-xylene and is described in, for example, U.S. Pat. No. 6,504,272, incorporated herein by reference. Where the methanol is used to alkylate naphthalene, this is conveniently effected in the presence of a catalyst comprising ZSM-5, MCM-22, PSH-3, SSZ-25, ERB-1, ITQ-1, ITQ-2, ITQ-13, MCM-36, MCM-49 or MCM-56. Such a process can be used to selectively produce 2,6-dimethylnaphthalene and is described in, for example, U.S. Pat. Nos. 4,795,847 and 5,001,295, incorporated herein by reference.

Where methanol or DME is used as an alkylating agent in the process of the invention, it can be provided as a separate feed to the process or can at least partly be generated in situ by adding a carbon dioxide-containing feed gas, such as a natural gas stream, to part or all of the effluent from the dehydrocyclization step. In particular, the dehydrocyclization effluent, prior to any separation of the aromatic components, can be fed to a reverse shift reactor and reacted with the carbon dioxide-containing feed under conditions to increase the carbon monoxide content of the effluent by reactions, such as Reactions 5 and 8 above.

In addition, methane and $CO_2$ and/or steam may be fed to a reverse shift reactor to generate syngas which can then be mixed with a portion of the dehydrocyclization effluent to adjust the $H_2/CO/CO_2$ ratios as required for the alkylation step.

Typically, the reverse shift reactor contains a catalyst comprising a transition metal on a support, such as Fe, Ni, Cr, Zn on alumina, silica or titania, and is operated under conditions including a temperature of about 500° C. to about 1200° C., such as about 600° C. to about 1000° C., for example about 700° C. to about 950° C. and a pressure of about 1 kPa to about 10,000 kPa, such as about 2,000 kPa to about 10,000 kPa, for example about 3000 kPa to about 5,000 kPa. Gas hourly space velocities may vary depending upon the type of process used, but generally the gas hourly space velocity of flow of gas through the catalyst bed is in the range of about 50 $hr^{-1}$ to about 50,000 $hr^{-1}$, such as about 250 $hr^{-1}$ to about 25,000 $hr^{-1}$, more preferably about 500 $hr^{-1}$ to about 10,000 $hr^{-1}$.

The effluent from the reverse shift reactor can then be fed to an alkylation reactor operating under conditions to cause reactions such as the following to occur:

$$CO+2H_2 \leftrightarrow CH_3OH \qquad \text{(Reaction 9)}$$

$$CH_3OH+C_6H_6 \rightarrow toluene+2H_2O \qquad \text{(Reaction 10)}$$

$$2CH_3OH+C_6H_6 \rightarrow xylenes+2H_2O \qquad \text{(Reaction 11)}$$

Suitable conditions for such an alkylation reactor would include a temperature of about 100 to about 700° C., a pressure of about 1 to about 300 atmospheres (100 to 30,000 kPa), and a WHSV for the aromatic hydrocarbon of about 0.01 to about 100 $hr^{-1}$. A suitable catalyst would comprise a molecular sieve having a constraint index of 1 to 12, such as ZSM-5, typically together with one or metals or metal oxides, such as copper, chromium and/or zinc oxide.

Preferably, where the alkylation catalyst includes a molecular sieve, the latter is modified to change its diffusion characteristics such that the predominant xylene isomer produced by Reaction 11 is paraxylene. Suitable means of diffusion modification include steaming and ex-situ or in-situ deposition of silicon compounds, coke, metal oxides, such as MgO, and/or P on the surface or in the pore mouths of the molecular sieve. Also preferred is that an active metal be incorporated into the molecular sieve so as to saturate more highly reactive species, such as olefins, which may be generated as by-products and which could otherwise cause catalyst deactivation.

The effluent from the alkylation reactor could then be fed to a separation section in which the aromatic products would initially be separated from the hydrogen and other low molecular weight materials, conveniently by solvent extraction. The aromatics products could then be fractionated into a benzene fraction, a toluene fraction, a $C_8$ fraction and a heavy fraction containing naphthalene and alkylated naphthalenes. The $C_8$ aromatic fraction could then be fed to a crystallization or sorption process to separate the valuable p-xylene component and the remaining mixed xylenes either sold as product or fed to an isomerization loop to generate more p-xylene. The toluene fraction could either be removed as saleable product, recycled to the alkylation reactor or fed to a toluene disproportionation unit, and preferably a selective toluene disproportionation unit for the preparation of additional p-xylene.

Aromatics Hydrogenation

In addition to or instead of the alkylation step, at least part of the aromatic components in the dehydrocyclization effluent can be hydrogenated to generate useful products such as cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). These products can be employed as fuels and chemical intermediates and, in the case of tetralin and decalin, can be used as the solvent for extracting the aromatic components from the dehydrocyclization effluent.

The hydrogenation is conveniently, but not necessarily, conducted after separation of the aromatic components from the dehydrocyclization effluent and conveniently employs part of the hydrogen generated by the dehydrocyclization reaction. Suitable aromatic hydrogenation processes are well known in the art and typically employ a catalyst comprising Ni, Pd, Pt, Ni/Mo or sulfided Ni/Mo supported on alumina or silica support. Suitable operating conditions for the hydrogenation process include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 $hr^{-1}$, such as about 2 to about 10 $hr^{-1}$.

Partial hydrogenation to leave one or more olefinic carbon-carbon bonds in the product may also be desirable so as to produce materials suitable for polymerization or other downstream chemical conversion. Suitable partial hydrogenation processes are well known in the art and typically employ a catalyst comprising noble metals with ruthenium being preferred supported on metallic oxides, such as $La_2O_3$—ZnO. Homogeneous noble metal catalyst systems can also be used. Examples of partial hydrogenation processes are disclosed in U.S. Pat. Nos. 4,678,861; 4,734,536; 5,457,251; 5,656,761; 5,969,202; and 5,973,218, the entire contents of which are incorporated herein by reference.

An alternative hydrogenation process involves low pressure hydrocracking of the naphthalene component to produce alkylbenzenes over a catalyst such as sulfided Ni/W or sulfided Ni supported on an amorphous aluminosilicate or a zeolite, such as zeolite X, zeolite Y or zeolite beta. Suitable operating conditions for low pressure hydrocracking include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 $hr^{-1}$, such as about 2 to about 10 $hr^{-1}$.

The invention will now be more particularly described with reference to the accompanying drawings and the following non-limiting Examples.

EXAMPLE 1

This example defines a metal oxide/carbide stability parameter that can be used to rank different metals according on their ability to form intrinsically stable metal oxide or carbide. Hence, it allows identification of potential candidate metals for forming stable metal oxide or carbide under dehydrocyclization reaction conditions. The metal oxide/carbide stability parameter is defined as follows:

$$S = \left(\frac{1}{n_{carbon}}\right)\Delta G_{f,carbide} - \left(\frac{1}{n_{oxygen}}\right)\Delta G_{f,oxide}$$

where S is the metal oxide/carbide stability parameter, $\Delta G_{f,carbide}$ is the standard Gibbs Energy of Formation for the metal carbide ($M_aC_b$), $n_{carbon}$ are the number of carbon atoms in the metal carbide (i.e., $n_{carbon}$=b), $\Delta G_{f,oxide}$ is the standard Gibbs Energy of Formation for the metal oxide ($M_xO_y$), and $n_{oxygen}$ are the number of oxygen atoms in the metal oxide (i.e., $n_{oxygen}$=y).

Based on the above definition, FIG. 1 shows the calculated value for the stability parameter for various metals. As the value of the stability parameter increases, it indicates higher stability of the metal oxide state relative to the metal carbide, hence making it increasingly difficult to convert the metals from its oxide to its carbide form. Since the degradation of a metal alloy under carburizing conditions at high temperatures is via the formation of metal carbides, this stability parameter provides a means of identifying metal oxides that are resistant to attack under dehydrocyclization conditions. Metals such as magnesium, barium, cerium and aluminum have very high stability parameters and hence, are suitable candidates as additives to metal alloys to form a protective surface metal oxide layer. Conversely, as the value to the stability parameter decreases, it indicates higher stability of the metal carbide state relative to the metal oxide state, hence making it increasingly difficult to convert the metals from its carbide to oxide form. Desirable metals are those having a metal oxide/carbide stability parameter greater than 300 kJ/mol.

EXAMPLE 2

Figure 2:
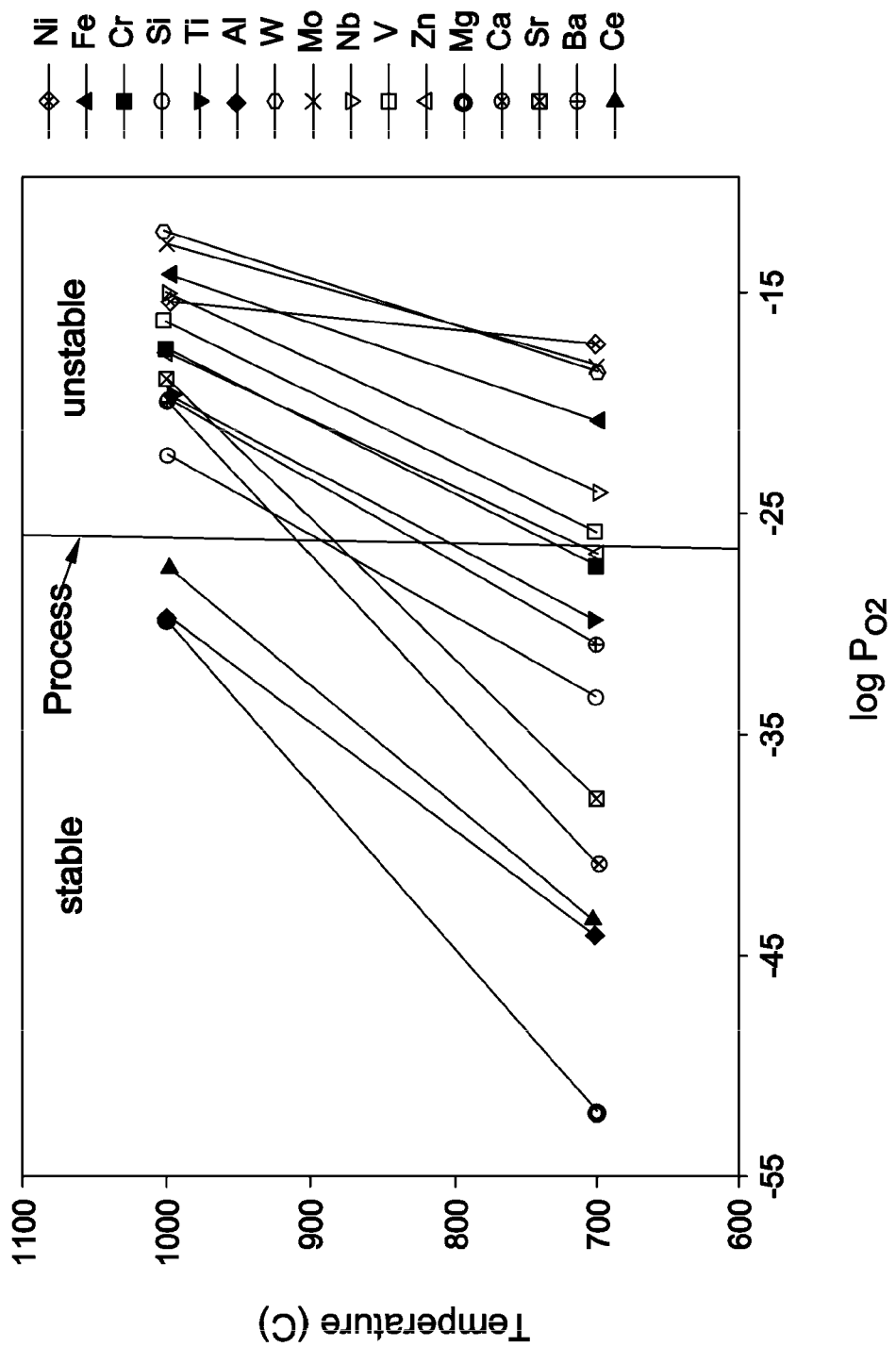
FIG. 2 is a graph plotting temperature against log $P_{O2}$ (where $P_{O2}$ is the oxygen partial pressure) for various metal oxides in the presence of a mixture of 40% $CH_4$, 50% $H_2$, 5% $C_6H_6$ and 5% CO.

Based on the conditions employed in the dehydrocyclization of methane and gas-solid equilibria, the stability of various metal oxides in the presence of 40% $CH_4$, 50% $H_2$, 5% $C_6H_6$ and 5% CO addition was determined over the temperature range of 700 to 1000° C. and the results are plotted in FIG. 2. Considering the equilibrium between the metal, metal oxide and metal carbide phases, FIG. 2 shows that oxides of aluminum, magnesium and cerium are stable over the entire span of dehydrocyclization conditions (consistent with their high stability parameter values S), whereas oxides of chromium, silicon and titanium are not stable. These results suggest that alloys containing aluminum, magnesium and/or cerium may be interesting candidates for dehydrocyclization service.

EXAMPLE 3

Figure 3:
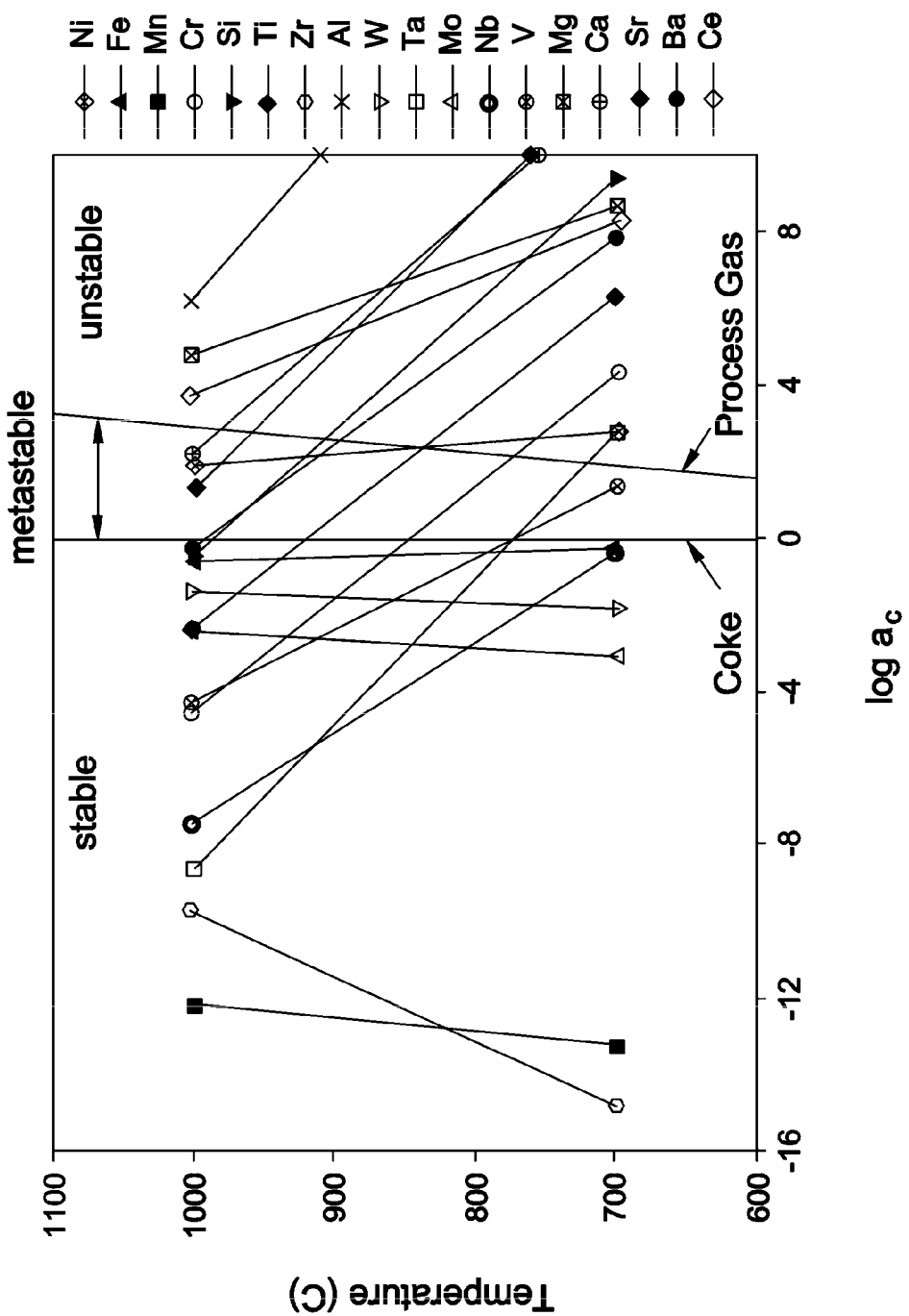
FIG. 3 is a graph plotting temperature against log $a_C$ (where $a_C$ is the carbon activity) for various metal carbides in the presence of a mixture of 40% $CH_4$, 50% $H_2$, 5% $C_6H_6$ and 5% CO.

Similarly the stability of various metal carbides in the presence of 40% $CH_4$, 50% $H_2$, 5% $C_6H_6$ and 5% CO addition was determined over the temperature range of 700 to 1000° C. and the results are plotted in FIG. 3. It is clear from FIG. 3 that carbides of molybdenum, tungsten and niobium are stable over the entire span of dehydrocyclization conditions and hence these metals should be able to form a stable surface carbide layer resistant to internal carbide formation.

Although zirconium is expected from FIG. 3 to form stable metal carbide, experimental results (based on a test described in Example 5) show that zirconium metal does not form a surface zirconium carbide layer. However, there is significant formation of internal zirconium hydride precipitates.

EXAMPLE 4

The alloys identified in Table 1 were tested to determine their carburization resistance under dehydrocyclization conditions by exposing small coupons (typically 0.5 cm long by 1.3 cm wide by 0.2 to 0.5 cm thick) of each alloy to a carburizing gas composed of an equimolar blend of methane and hydrogen at 900° C. for 168 hours. Prior to the carburization test, the surface of each coupon was bead-blasted to remove any surface oxide layer and to ensure the samples had similar surface roughness characteristics. The carburization resistance was determined by measuring the carbon uptake (in units of grams divided by the number of square meters of exposed superficial surface area of the coupon) by weighing the coupon before and after the test. The carbon uptake was confirmed using scanning electron microscopy to verify internal metal carbide formation and the extent of the underlying carburization zone.

Figure 4:
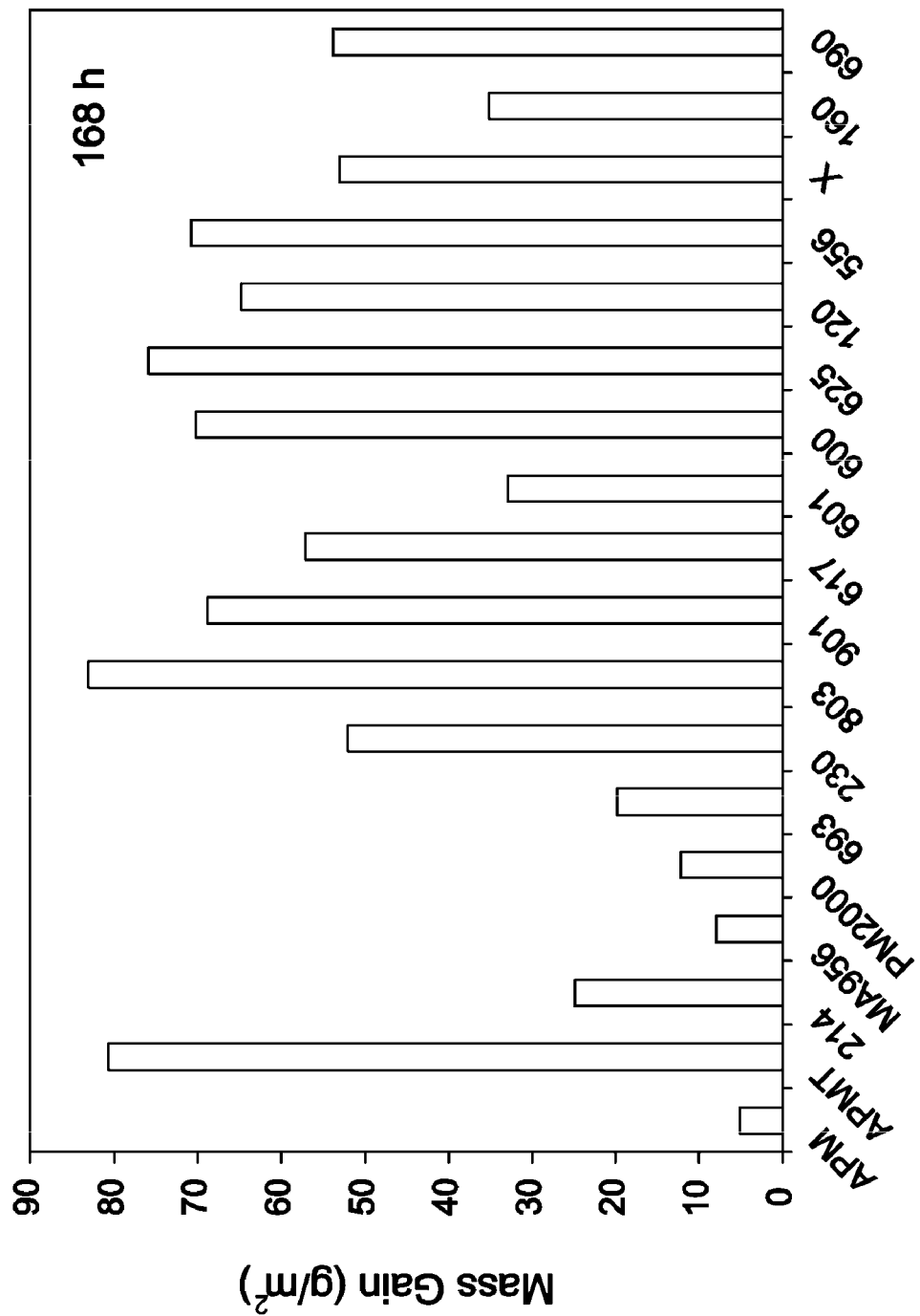
FIG. 4 is a bar graph showing the mass gain in g/m² for various metal alloys after exposure to an equimolar mixture of methane and hydrogen at 900° C. for 168 hours.
Figure 5:
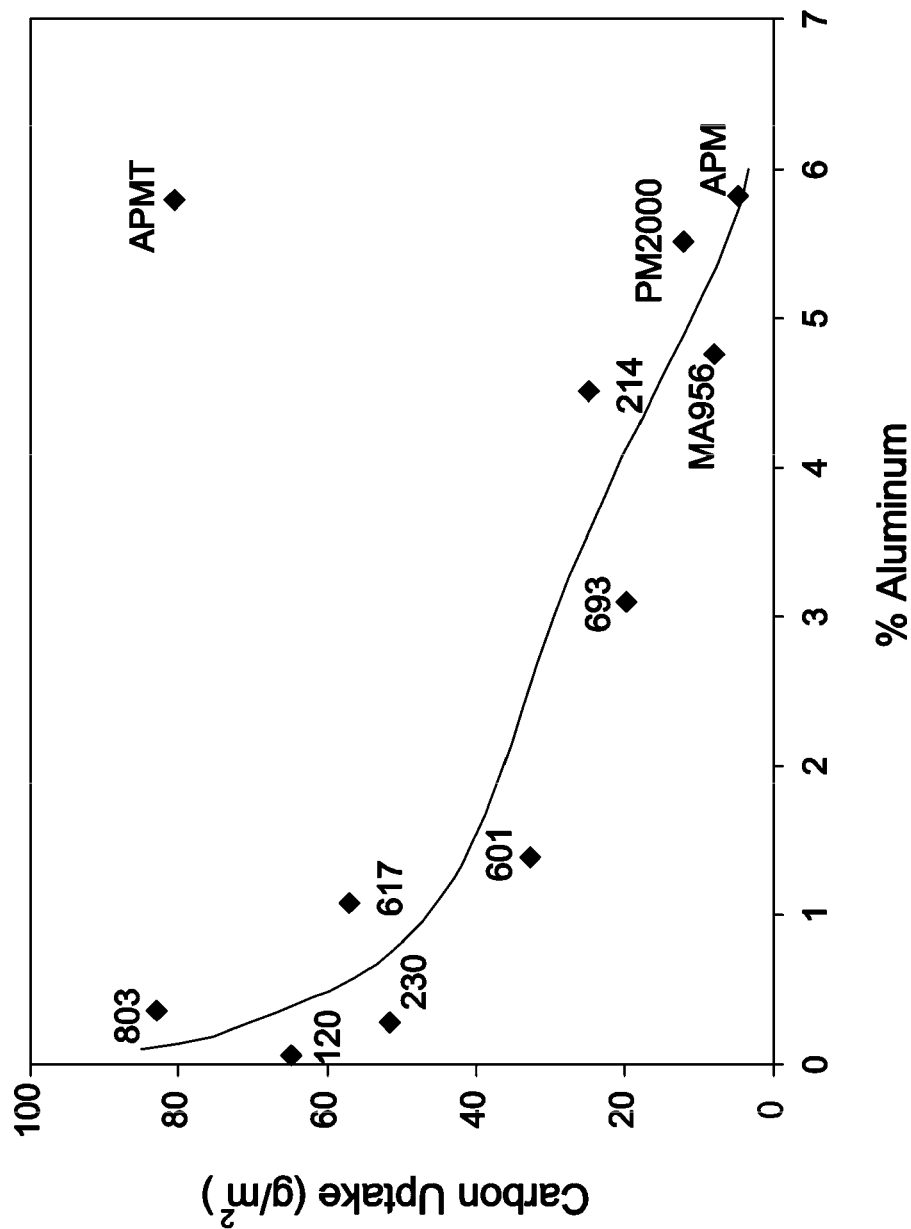
FIG. 5 is a graph plotting mass gain in g/m² against weight % aluminum content for various metal alloys after exposure to an equimolar mixture of methane and hydrogen at 900° C. for 168 hours.

The results are shown in FIGS. 4 and 5, from which it will be seen that:
- Iron-based alloys Kanthal® APM (5.8 weight % aluminum), Incoloy® MA956 (4.75 weight % aluminum) and ODS alloy PM2000 (5.5 weight % aluminum) showed the highest resistance to carbon uptake.
- Nickel-based alloys Haynes® alloy 214 (4.5 weight % aluminum) and Inconel® alloy 693 (3.1 weight % aluminum) showed moderate resistance to carbon uptake.
- Conventional high temperature alloys, containing varying proportions of nickel, iron and chromium (such as Incoloy® 803 used for steam cracking applications) showed poor carburization performance with very high carbon uptakes (typically in the range of 45-85 g/m$^2$).
- With the exception of Kanthal® APMT (which also contains molybdenum), carbon uptake decreases significantly as the aluminum content of the alloy increases.
- Aluminum-containing alloys, which were identified to have the highest carburization resistance (e.g., Kanthal® APM), showed resistance to carbon uptake even in the absence of surface protective aluminum oxide layer (since these coupons were bead-blasted). It is therefore noted that the presence of protective oxide layer (although may improve carburization resistance) is not necessary for these alloys to show resistance to carbon uptake.

EXAMPLE 5

Figure 6:
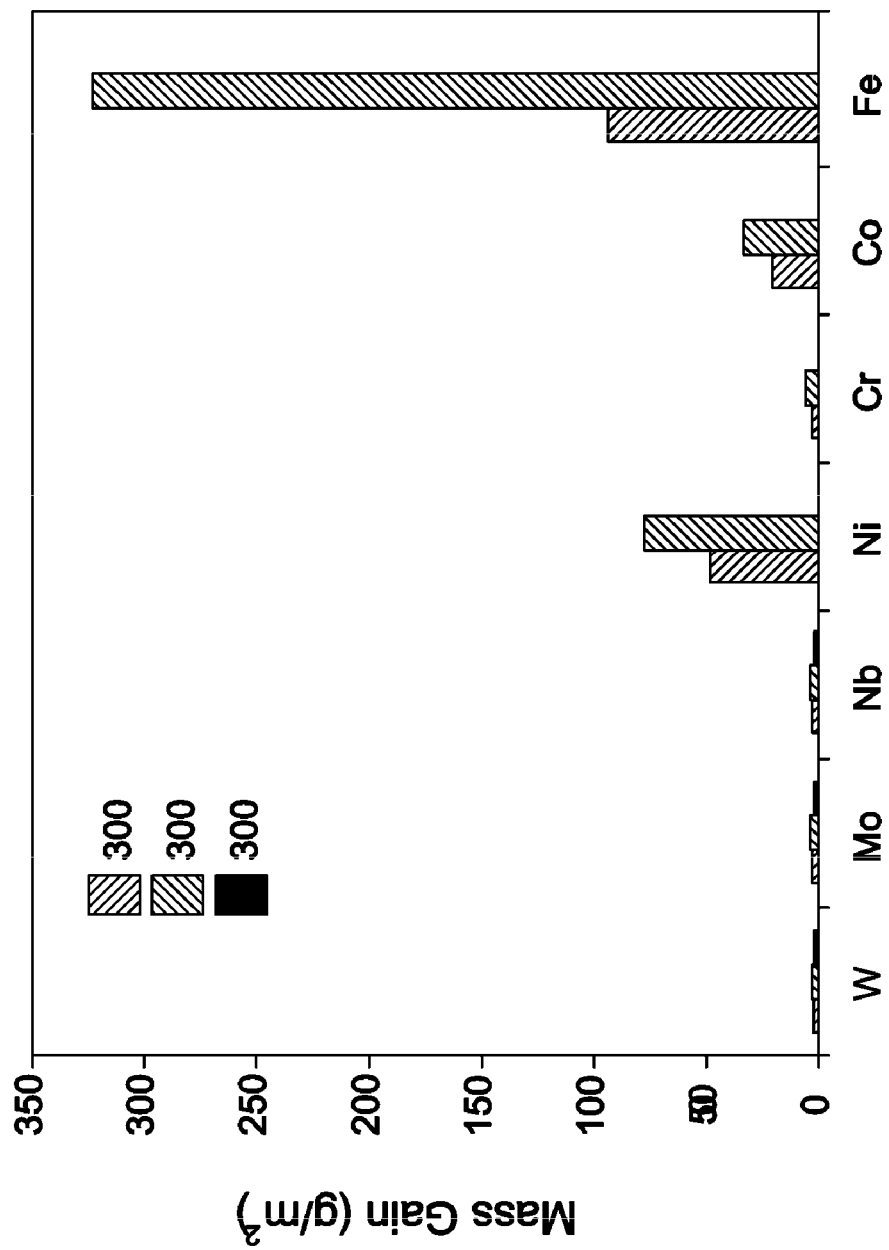
FIG. 6 is a bar graph showing the mass gain in g/m² for various metals after exposure to an equimolar mixture of methane and hydrogen at 900° C. for between 24 and 336 hours.

The test described in Example 4 was repeated to determine the carburization resistance under dehydrocyclization conditions of a plurality of different refractory metals and the results of exposure to the methane/hydrogen blend at 900° C. for 24, 168 and 336 hours are shown in FIG. 6. It was found that the surface carbide layer formed on each of the molybdenum, tungsten, niobium and chromium coupons prevented further carbon ingress, thereby resulting in excellent carburization resistance. Moreover, the carbide passivation layer formed on these metals showed very low surface coke deposition, which may provide a method of mitigating coke deposition at exposed heat-transfer surfaces. In contrast, the nickel, iron and cobalt coupons exhibited significant carbon uptake.

EXAMPLE 6

The metal coupons, after exposure to the methane/hydrogen blend at 900° C. for 24 hours according to the test of Example 4, were exposed to air at 700° C. for 6 hours. The molybdenum, tungsten, and chromium coupons showed good oxidation resistance (less than 1% weight loss) as well as good carburization resistance, whereas the niobium coupon exhibited significantly lower oxidation resistance (about 5% weight loss).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

TABLE 1

|     | APM | APMT | 214 | MA956 | PM2000 | 693 | 230 | 803 | 901 | 617 |
|-----|-----|------|-----|-------|--------|-----|-----|-----|-----|-----|
| Ni    | 0   | 0    | 75  | 0.5   | 0      | 62  | 57  | 34  | 43  | 44.5 |
| Fe    | 72  | 72   | 3   | 74    | 74     | 4   | 3   | 36  | 36  | 3   |
| Cr    | 22  | 22   | 16  | 20    | 20     | 29  | 22  | 27  | 13  | 22  |
| Al    | 5.8 | 5.8  | 4.5 | 4.75  | 5.5    | 3.1 | 0.3 | 0.4 | 0.4 | 1.1 |
| Mo    |     | 3    |     |       |        |     |     |     | 6   | 9   |
| Co    |     |      |     |       |        |     |     |     |     |     |
| Other |     |      |     |       | 0.5Y   |     | 14W |     | 3Ti |     |

|     | 601 | 600  | 625  | 120 | 556 | X   | 160 | 690 | 800HT |
|-----|-----|------|------|-----|-----|-----|-----|-----|-------|
| Ni    | 61  | 72   | 58   | 37  | 20  | 47  | 37  | 58  | 33    |
| Fe    | 13  | 8    | 5    | 33  | 31  | 18  | 2   | 9   | 40    |
| Cr    | 23  | 15.5 | 21.5 | 25  | 22  | 22  | 28  | 29  | 21    |
| Al    | 1.4 |      |      | 0.1 |     |     |     |     |       |
| Mo    |     |      | 9    | 2.5 | 3   |     |     |     |       |
| Co    |     |      |     | 3    | 18  | 1.5 | 29  |     |       |
| Other |     |      | 4Nb  |     |     |     | 3Si |     |       |

The invention claimed is:

1. A process for converting methane to higher hydrocarbons including aromatic hydrocarbons, the process comprising contacting a feed containing methane with a dehydrocyclization catalyst in a reaction zone under conditions effective to convert said methane to aromatic hydrocarbons, wherein said reaction zone is contained within a reactor and wherein the reactor or an internal component of the reactor has at least one surface that is chemically exposed to said feed and is formed from a refractory material wherein said at least one surface is formed from a refractory alloy that exhibits a carbon uptake (mass of carbon absorbed per unit of exposed metal surface area) of less than 25 g/m$^2$ when exposed to mixture of 50 vol% methane and 50 vol% $H_2$ at 900° C. for 168 hours, said at least one surface further characterized by having a surface carbide layer formed thereon either (i) during the dehydrocyclization reaction with a methane feed, or (ii) by pre-carburizing said surface by exposing said surface to a carbon-containing atmosphere.

2. The process of claim 1, wherein said at least one surface is formed from a refractory material that exhibits a carbon uptake (mass of carbon absorbed per unit of exposed metal surface area) of less than 15 g/m$^2$ when exposed to mixture of 50 vol% methane and 50 vol% $H_2$ at 900° C. for 168 hours.

3. The process of claim 1, wherein said at least one surface is formed from a refractory material that exhibits a carbon uptake (mass of carbon absorbed per unit of exposed metal surface area) of less than 10 g/m$^2$ when exposed to mixture of 50 vol% methane and 50 vol% $H_2$ at 900° C. for 168 hours.

4. The process of claim 1, wherein said at least one surface is formed from a refractory metal or alloy that comprises, or is capable of forming under said conditions, a continuous oxide or carbide layer stable under said conditions.

5. The process of claim 1, wherein said at least one surface is formed from a refractory metal or alloy comprising of a metal having a metal oxide/carbide stability parameter (S) greater than 300 kJ/mol.

6. The process of claim 1, wherein said at least one surface is formed from a refractory alloy containing at least 0.5 weight% of at least one of aluminum, magnesium or cerium.

7. The process of claim 1, wherein said at least one surface is formed of a refractory metal or alloy comprising molybdenum, tungsten, chromium and/or niobium.

8. The process of claim 1, wherein said at least one surface is chemically exposed to said feed through a refractory, abrasion resistant coating.

9. The process of claim 8, wherein said refractory, abrasion resistant coating comprises at least one of a ceramic, phosphide, nitride, carbide, and oxide.

10. The process of claim 1, wherein said at least one surface comprises a surface of an internal component of the reactor.

11. The process of claim 1, wherein said at least one surface is formed from a refractory alloy containing at least 0.5 weight% of at least one of aluminum, magnesium, yttrium, silicon, or cerium.

12. The process of claim 1, wherein said at least one surface is formed from an iron-based alloy.

13. The process of claim 1, wherein said at least one surface is formed from a nickel-based alloy.

14. The process of claim 1, wherein said at least one surface is formed from a cobalt-based alloy.

15. The process of claim 1, wherein said conditions include a temperature from about 600° C. to about 1000° C.

16. The process of claim 1, wherein said conditions include a temperature from about 800° C. to about 950° C.

17. The process of claim 1, wherein said conditions include a pressure of about 30 kPa to about 700 kPa.

18. The process of claim 1, wherein said feed also contains $H_2$, $H_2O$, CO and/or $CO_2$.

19. The process of claim 1, wherein said dehydrocyclization catalyst comprises a metal or compound thereof on an inorganic support, and further wherein said dehydrocyclization catalyst comprises at least one of molybdenum, tungsten, zinc and rhenium or a compound thereof on ZSM-5, silica or an aluminum oxide.

* * * * *